US012797581B2

(12) United States Patent
Kaneko

(10) Patent No.: US 12,797,581 B2
(45) Date of Patent: Nov. 17, 2026

(54) CATHETER HANDLE AND CATHETER WITH THE SAME

(71) Applicant: KANEKA CORPORATION, Osaka (JP)

(72) Inventor: Takuya Kaneko, Okaya (JP)

(73) Assignee: KANEKA CORPORATION, Osaka (JP)

( * ) Notice: Subject to any disclaimer, the term of this patent is extended or adjusted under 35 U.S.C. 154(b) by 366 days.

(21) Appl. No.: 18/607,674

(22) Filed: Mar. 18, 2024

(65) Prior Publication Data

US 2024/0216647 A1 Jul. 4, 2024

Related U.S. Application Data

(63) Continuation of application No. PCT/JP2022/034434, filed on Sep. 14, 2022.

(30) Foreign Application Priority Data

Dec. 13, 2021 (JP) ................................ 2021-201977
Mar. 24, 2023 (JP) ................................ 2023-047542
Mar. 24, 2023 (JP) ................................ 2023-047543

(51) Int. Cl.
*A61M 25/01* (2006.01)

(52) U.S. Cl.
CPC .... *A61M 25/0136* (2013.01); *A61M 25/0147* (2013.01)

(58) Field of Classification Search
None
See application file for complete search history.

(56) References Cited

U.S. PATENT DOCUMENTS 5,334,145 A * 8/1994 Lundquist ......... A61M 25/0147 604/95.04
2002/0143378 A1* 10/2002 Nguyen ............ A61M 25/0136 607/116

(Continued)

FOREIGN PATENT DOCUMENTS

JP 2015-523892 A 8/2015
JP 2018-506333 A 3/2018
JP 2018-515215 A 6/2018

OTHER PUBLICATIONS

International Search Report (PCT/ISA/210), issued in PCT/JP2022/034434, dated Dec. 6, 2022.

*Primary Examiner* — Manuel A Mendez
(74) *Attorney, Agent, or Firm* — Birch, Stewart, Kolasch & Birch, LLP

(57) ABSTRACT

A catheter handle including a handle body; a shaft disposed in and fixed to the handle body; a slider disposed on an outside of the shaft, having a first engagement part extending spirally on an outer surface thereof, and displaceable in an axial direction along the shaft; a rotary knob rotatable around the axial direction relative to the handle body, and having a second engagement part on an inner surface thereof, which engages with the first engagement part; a linear member having a first and second portion disposed in a lumen of a tube and an intermediate portion therebetween, the intermediate portion disposed in the interior of the handle body; and a return guide contacting the intermediate portion of the linear member. The linear member is fixed to the slide at a part of the linear member on the first portion side from a contacting part with the return guide.

16 Claims, 8 Drawing Sheets

(56) References Cited

U.S. PATENT DOCUMENTS

| | | | | |
|---|---|---|---|---|
| 2006/0142694 | A1* | 6/2006 | Bednarek .......... | A61M 25/0136 604/95.04 |
| 2008/0091169 | A1* | 4/2008 | Heideman ......... | A61M 25/0012 604/528 |
| 2015/0231366 | A1* | 8/2015 | Davies .............. | A61M 25/0136 604/95.04 |
| 2016/0082226 | A1* | 3/2016 | Eversull ............ | A61M 25/0147 604/95.04 |
| 2016/0206853 | A1 | 7/2016 | Bolduc et al. | |
| 2016/0325076 | A1 | 11/2016 | Terwey | |
| 2018/0304044 | A1 | 10/2018 | Eversull et al. | |
| 2019/0111239 | A1 | 4/2019 | Bolduc et al. | |
| 2020/0139083 | A1 | 5/2020 | Terwey | |
| 2021/0001087 | A1 | 1/2021 | Davies et al. | |

* cited by examiner

[Fig. 1]
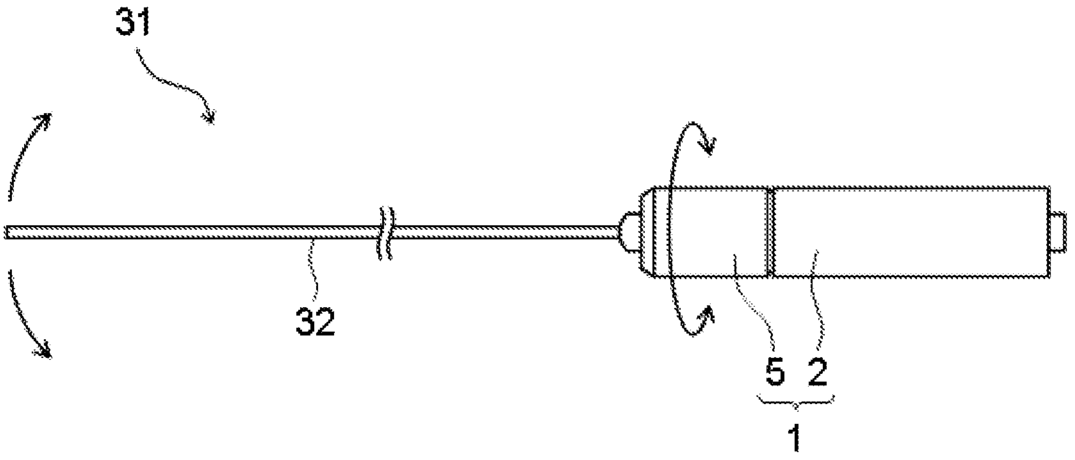
[Fig. 2]
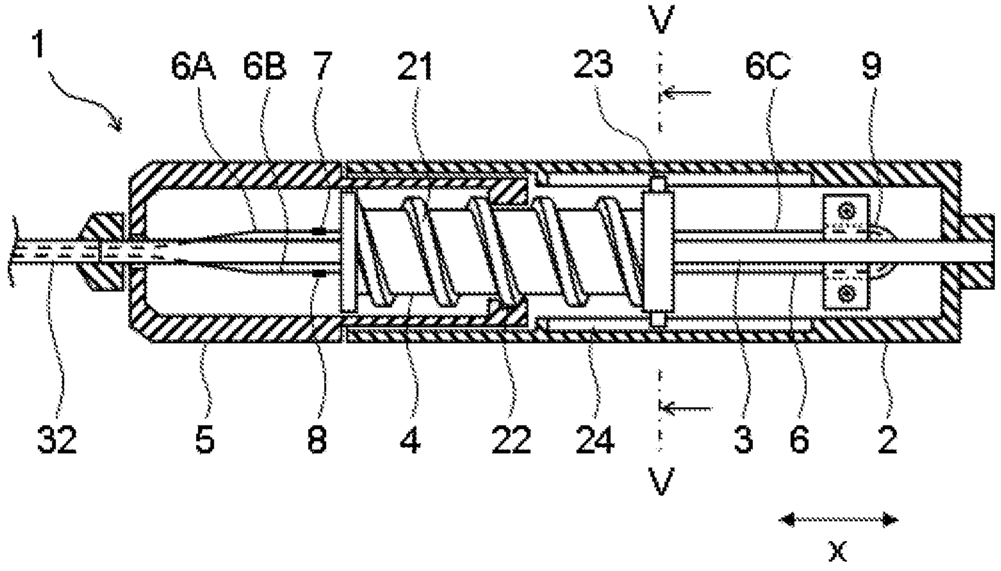

[Fig. 3]
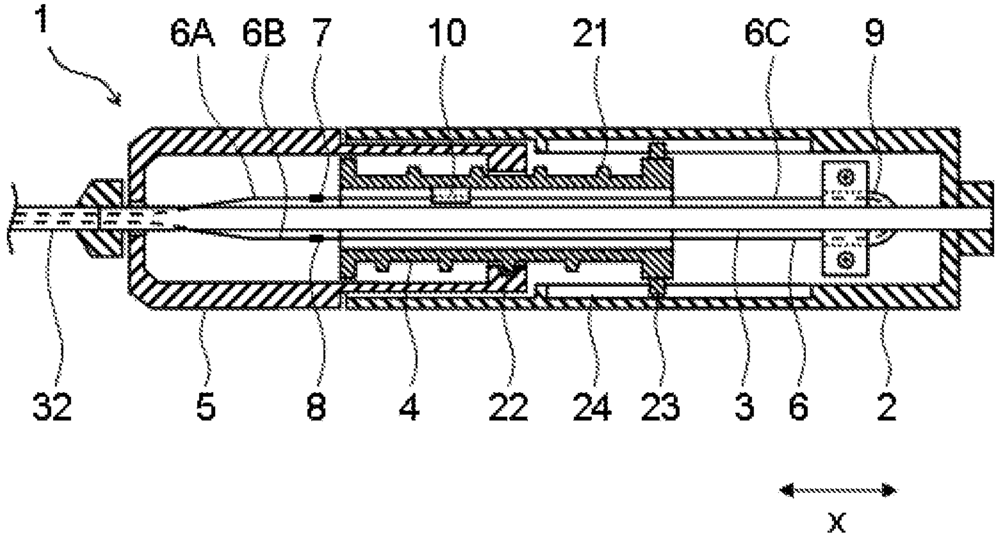
[Fig. 4]
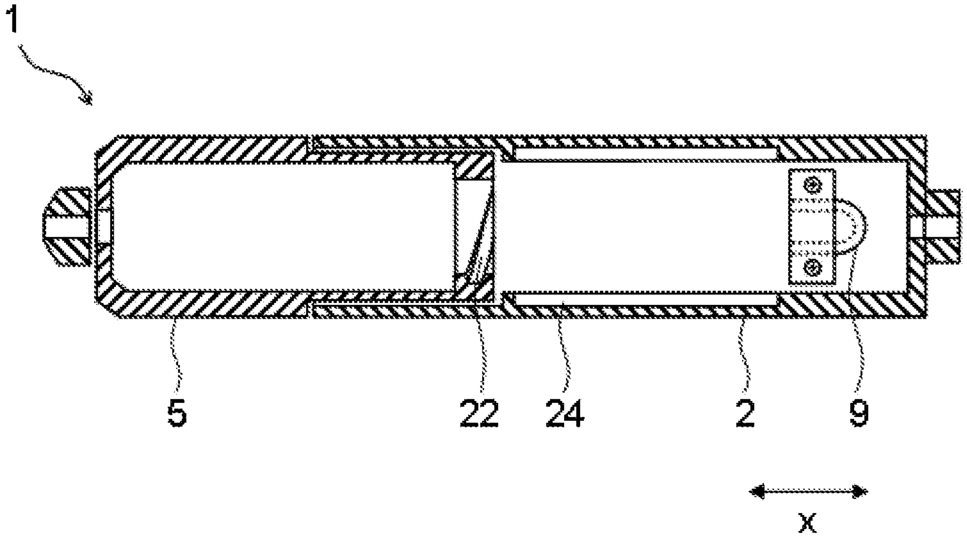

[Fig. 5]
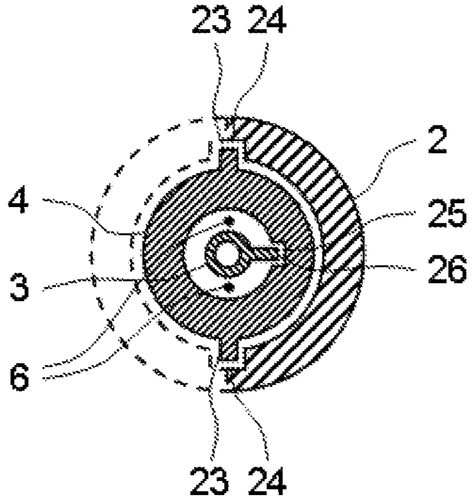

[Fig. 6]
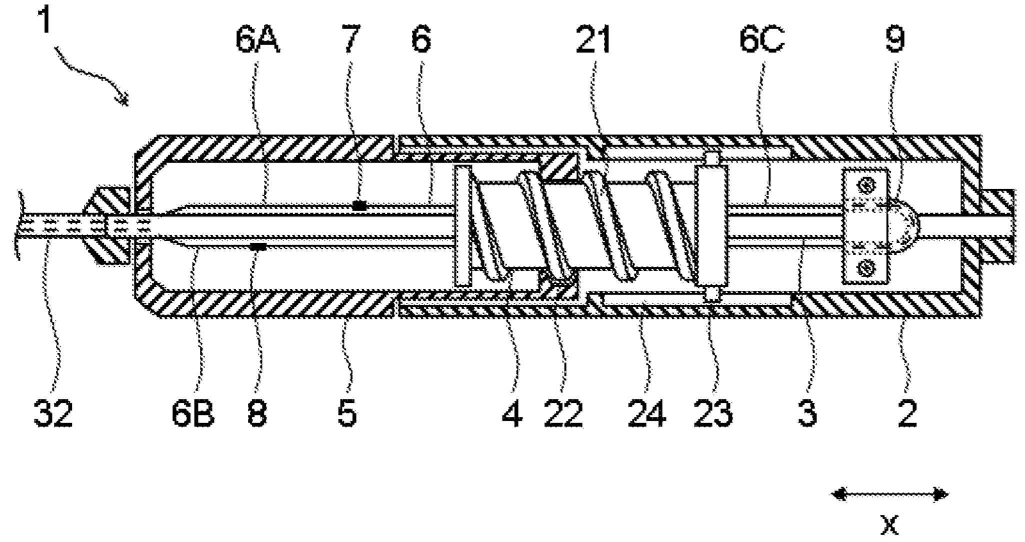
[Fig. 7]
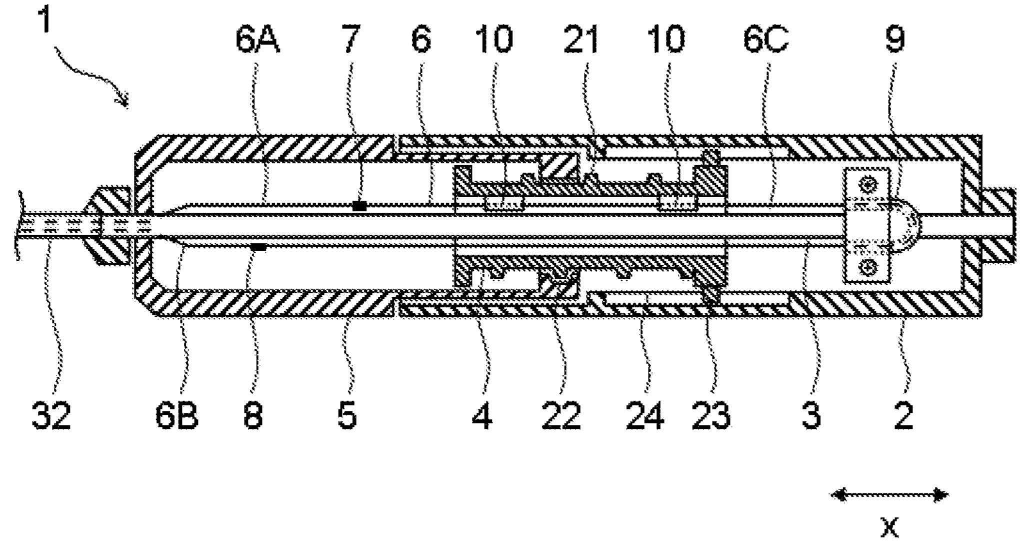

[Fig. 8]
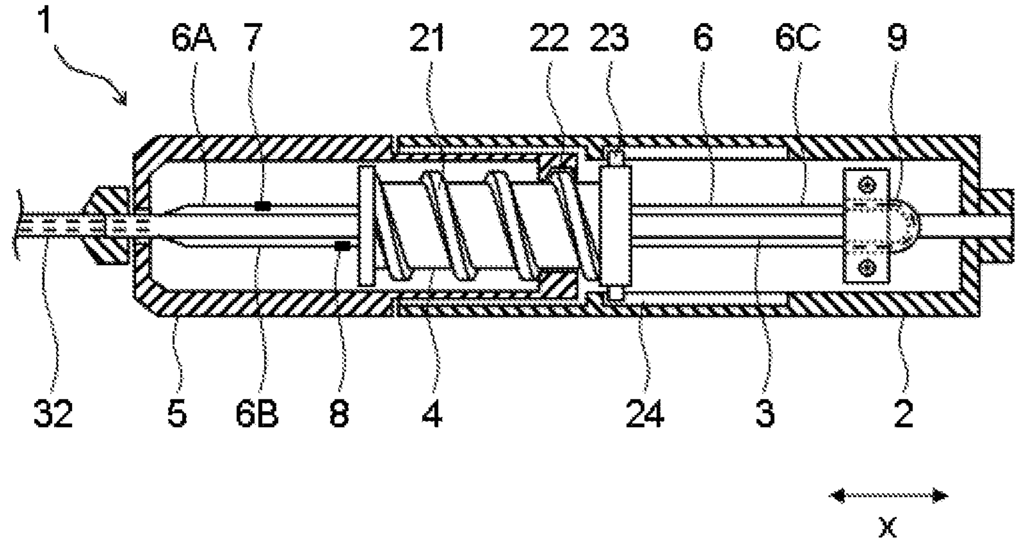
[Fig. 9]
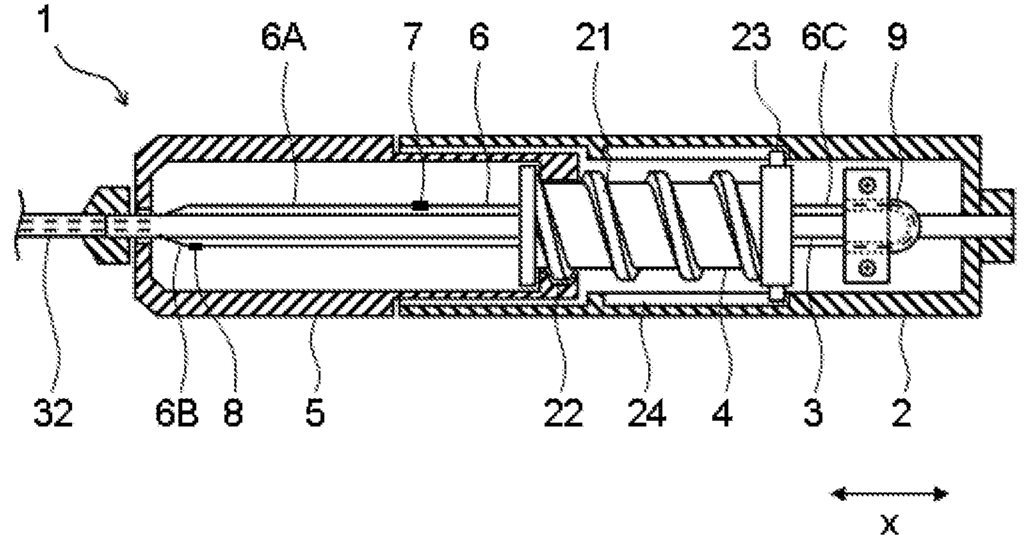

[Fig. 10]
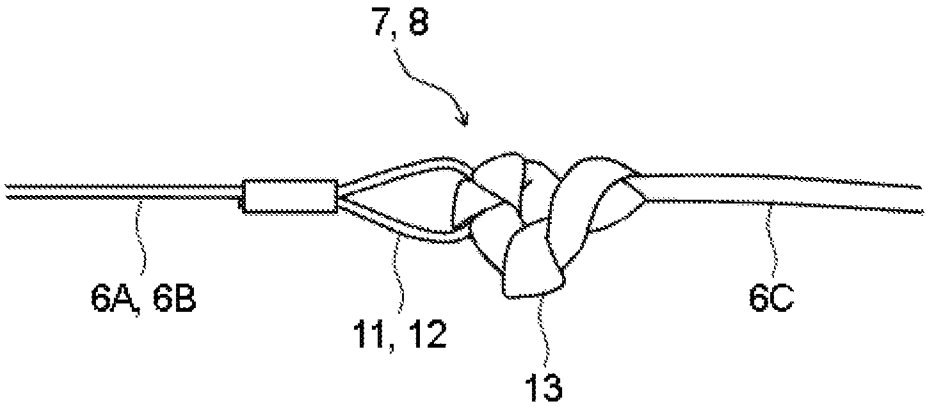
[Fig. 11]
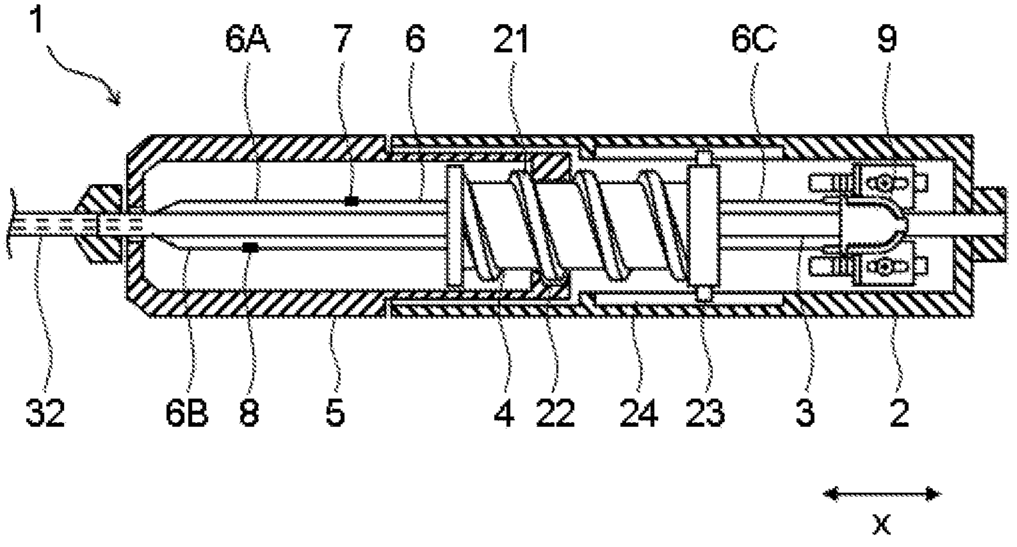

[Fig. 12]
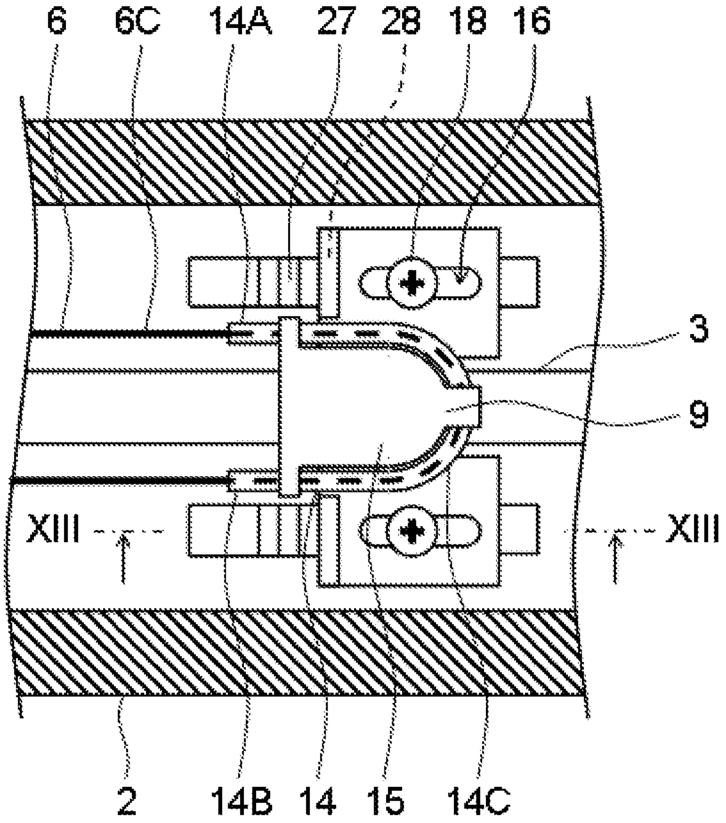
[Fig. 13]
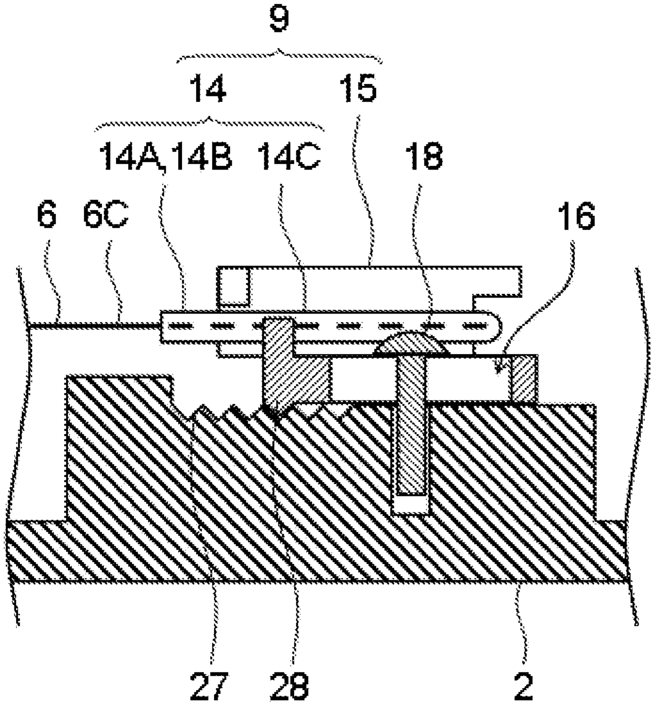

[Fig. 14]
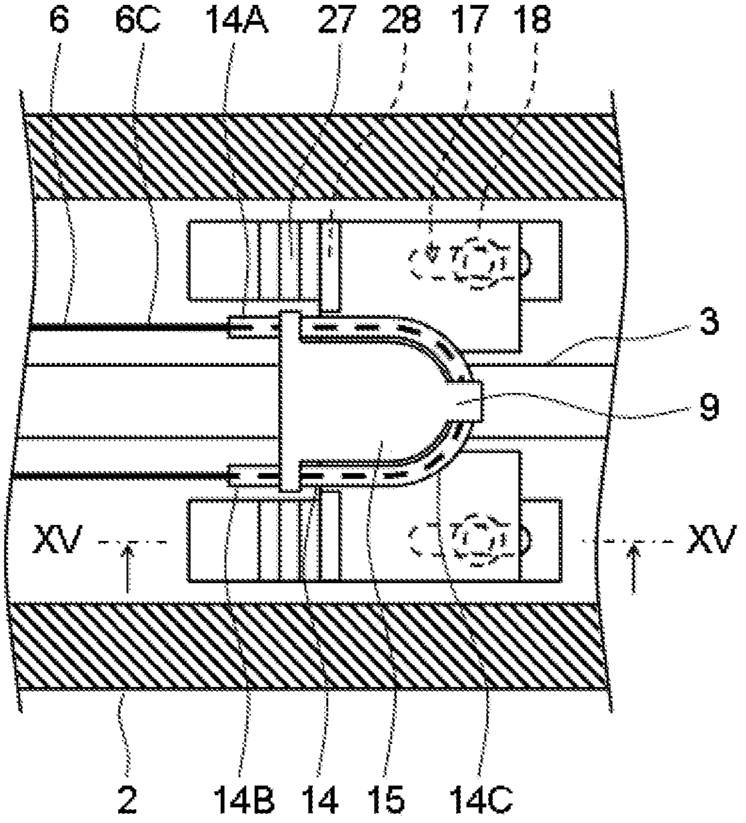
[Fig. 15]
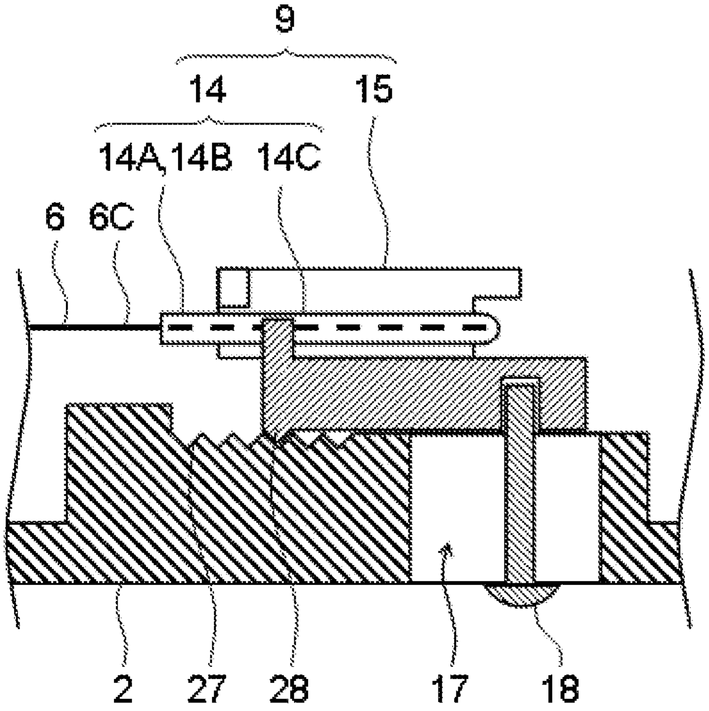

CATHETER HANDLE AND CATHETER WITH THE SAME

CROSS REFERENCE TO RELATED APPLICATIONS

This application is a Continuation of PCT International Application No. PCT/JP2022/034434, filed on Sep. 14, 2022, which claims priority under 35 U.S.C. 119(a) to Patent Application Nos. 2021-201977, filed in Japan on Dec. 13, 2021; 2023-047542, filed in Japan on Mar. 24, 2023; and 2023-047543, filed in Japan on Mar. 24, 2023, all of which are hereby expressly incorporated by reference into the present application.

TECHNICAL FIELD

The present invention relates to a handle used for a catheter and a catheter equipped with the handle.

BACKGROUND ART

A catheter usually comprises a tube for inserting into a body cavity such as a blood vessel, a digestive tract and an ureter tract, and a handle provided on a proximal side of the tube. Catheters in which a distal end part of the tube can be bent by operating the handle on the proximal side are known. In such catheters, a wire is disposed in a lumen of the tube, a distal end part of the wire is fixed to the distal end part of the tube, a proximal end of the wire is connected to the handle, and the distal end part of the tube can be bent by operating the handle. For example, in a catheter with two wires disposed in the lumen of the tube, the distal end part of the tube can be bent to one side by pulling one of the two wires proximally and to another side by pulling the other thereof by operating the handle.

As such a catheter handle, for example, Patent Literature 1 discloses a catheter handle, which includes two control wires, and a distal end part of which is coupled to a catheter at a distal region thereof, the handle comprising: a housing; a slide assembly positioned within the housing and operable to translate linearly therein; and a control knob rotatably coupled to the housing; wherein a proximal portion of each of the two control wires is disposed in the housing; linearly translating the slide assembly enables the slide assembly to separately manipulate each of the two control wires; rotation of the control knob in a first rotational direction causes the slide assembly to tension one of the two control wires thereby effecting a change in deflection of the catheter in a first deflection direction; and rotation of the control knob in a second rotational direction causes the slide assembly to tension the other of the two control wires thereby effecting a change in deflection of the catheter in a second deflection direction. Patent Literature 2 discloses a catheter handle for deflecting a distal part of a catheter, the handle comprising: a first rotating member having a first diameter and to which a first wire is connected; a second rotating member having a second diameter smaller than the first diameter and to which a second wire is connected; wherein the second rotating member is coupled to the first rotating member such that a center point of the second rotating member is offset from a center point of the first rotating member; the first and second rotating members are configured such that rotation of the first rotating member via the first wire rotates the second rotating member and the second wire to deflect the distal part of the catheter.

CITATION LISTS

Patent Literatures

Patent Literature 1

Japanese Unexamined Laid-open Patent Application Publication No. 2015-523892

Patent Literature 2

Japanese Unexamined Laid-open Patent Application Publication No. 2018-515215

SUMMARY OF INVENTION

Technical Problem

As described above, various catheter handles have been conventionally proposed, and an object of the present invention is to provide a catheter handle with a novel structure and a catheter equipped with the handle.

Solution to Problem

The present invention includes the following catheter handle and catheter.

[1] A catheter handle for operating a tube of a catheter, comprising: a handle body having an inner cavity extending in an axial direction; a shaft disposed in the inner cavity of the handle body, extending in the axial direction, and fixed to the handle body; a slider disposed on an outside of the shaft, having a first engagement part extending spirally on an outer surface of the slider, and configured so as to be displaceable in the axial direction along the shaft; a rotary knob provided so as to be rotatable around the axial direction relative to the handle body, and having a second engagement part on an inner surface of the rotary knob, which engages with the first engagement part of the slider; a linear member having a first end and a second end, and having a first portion including the first end, a second portion including the second end, and an intermediate portion between the first portion and the second portion, the first portion and the second portion being disposed in a lumen of the tube, and the intermediate portion being disposed in the inner cavity of the handle body; and a return guide provided in the inner cavity of the handle body and being in contact at a contacting part of the linear member with at least a part of the intermediate portion of the linear member; wherein the linear member is fixed to the slider at a part of the linear member on the first end side from the contacting part of the linear member with the return guide.

[2] The catheter handle according to [1] above, wherein, in the linear member, the intermediate portion is made of a material different from the first portion and the second portion.

[3] The catheter handle according to [1] or [2] above, wherein the intermediate portion has lower bending rigidity than the first portion and the second portion.

[4] The catheter handle according to any one of [1] to [3] above, wherein the intermediate portion is composed of a rope.

[5] The catheter handle according to any one of [1] to [4] above, wherein the first portion and the second portion are composed of a metal wire, and the intermediate portion is composed of a fiber rope.

[6] The catheter handle according to any one of [1] to [5] above, wherein one of the first engagement part and the second engagement part is a convex part and the other of the first engagement part and the second engagement part is a groove.

[7] The catheter handle according to any one of [1] to [6] above, wherein a proximal part of the first portion is connected to the intermediate portion at a first connecting part, a proximal part of the second portion is connected to the intermediate portion at a second connecting part, and the first connecting part and the second connecting part are located distal to a distal end of the slider in a state where the slider is displaced to a most distal side.

[8] The catheter handle according to any one of [1] to [7] above, wherein a proximal end of the first portion has a first annular part formed in an annular shape, and an end part of the intermediate portion on the first portion side is tied to the first annular part, thereby forming a first connecting part, and a proximal end of the second portion has a second annular part formed in an annular shape, and an end part of the intermediate portion on the second portion side is tied to the second annular part, thereby forming a second connecting part.

[9] The catheter handle according to [8] above, wherein a knot formed by tying the end part of the intermediate portion on the first portion side to the first annular part and a knot formed by tying the end part of the intermediate portion on the second portion side to the second annular part are hardened with an adhesive or melt-solidified.

[10] The catheter handle according to any one of [1] to [9] above, wherein the intermediate portion is fixed to the slider at least at a distal one-third part of the slider.

[11] The catheter handle according to any one of [1] to [9] above, wherein the intermediate portion is fixed to the slider at least at a distal one-third part and a proximal one-third part of the slider.

[12] The catheter handle according to any one of [1] to [11] above, wherein the return guide is located proximal to the slider and configured to be fixable to the handle body at different positions in the axial direction.

[13] The catheter handle according to [12] above, wherein an elongated hole extending in the axial direction is formed in the return guide, and a fixture for fixing the return guide is inserted through the elongated hole and is fitted or screwed into the handle body.

[14] The catheter handle according to [12] above, wherein an elongated hole extending in the axial direction is formed in the handle body, and a fixture for fixing the return guide is inserted through the elongated hole and is fitted or screwed into the return guide.

[15] The catheter handle according to any one of [12] to [14] above, wherein the return guide comprises a guiding tube through which the intermediate portion of the linear member is inserted and which is arranged in a shape convex toward the proximal side, and a holding member which holds the guiding tube, and the holding member is configured to be fixable to the handle body at different positions in the axial direction.

[16] The catheter handle according to [15] above, wherein the guiding tube has a first section including one end, a second section including the other end, and a third section between the first section and the second section, at least a part of the third section is held by the holding member, and the first section and the second section are not held by the holding member, and extend substantially parallel to the axial direction distally from the holding member in a plan view where the guiding tube is seen in the shape convex toward the proximal side.

[17] The catheter handle according to any one of [1] to [16] above, wherein the slider has a third engagement part on the outer surface of the slider, the handle body has a fourth engagement part on an inner surface of the handle body, which engages with the third engagement part, and at least one of the third engagement part and the fourth engagement part is provided so as to extend in the axial direction.

[18] The catheter handle according to any one of [1] to [17] above, wherein the slider has a fifth engagement part on an inner surface of the slider, the shaft has a sixth engagement part on an outer surface of the shaft, which engages with the fifth engagement part, and at least one of the fifth engagement part and the sixth engagement part is provided so as to extend in the axial direction.

[19] A catheter comprising: a catheter handle according to any one of [1] to [18] above; and a tube provided on a distal side of the catheter handle.

Advantageous Effects of Invention

According to the catheter handle and catheter of the present invention, the tube provided on the distal side of the catheter handle can be operated by rotating the rotary knob.

BRIEF DESCRIPTION OF DRAWINGS

FIG. 1 shows an overall view of a catheter provided with a catheter handle.

FIG. 2 shows a plan view of an embodiment of the internal structure of the catheter handle provided in the catheter shown in FIG. 1.

FIG. 3 shows a plan view of the internal structure of the catheter handle shown in FIG. 2 with a slider partially cut away along an axial direction.

FIG. 4 shows a plan view of the internal structure of the catheter handle shown in FIG. 2 with a slider and a shaft removed.

FIG. 5 shows a cross-sectional view taken along a line V-V of the catheter handle shown in FIG. 2.

FIG. 6 shows a plan view of another embodiment of the internal structure of the catheter handle provided in the catheter shown in FIG. 1.

FIG. 7 shows a plan view of the internal structure of the catheter handle shown in FIG. 6 with a slider partially cut away along the axial direction.

FIG. 8 shows a plan view of the catheter handle shown in FIG. 6 in the state where the slider displaced to a most distal side.

FIG. 9 shows a plan view of the catheter handle shown in FIG. 6 in the state where the slider displaced to a most proximal side.

FIG. 10 shows a configuration example of a first connecting part and a second connecting part.

FIG. 11 shows a plan view of still another embodiment of the internal structure of the catheter handle provided in the catheter shown in FIG. 1.

FIG. 12 shows an enlarged plan view around a return guide in the catheter handle shown in FIG. 11.

FIG. 13 shows a cross-sectional view taken along a line XIII-XIII around the return guide shown in FIG. 12.

FIG. 14 shows an enlarged plan view of a modified example around the return guide shown in FIG. 11.

FIG. 15 shows a cross-sectional view taken along a line XV-XV around the return guide shown in FIG. 14.

DESCRIPTION OF EMBODIMENTS

Hereinafter, a catheter handle and a catheter equipped with the handle of the present invention is specifically explained below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

The overall structure of a catheter equipped with a catheter handle is explained with reference to FIG. 1. A catheter 31 according to an embodiment of the present invention comprises a catheter handle 1 (hereinafter may be referred to as "handle 1") and a tube 32 provided on a distal side of the handle 1. The catheter 31 is used for, for example, treatment or examination by inserting the tube 32 into a body cavity such as a blood vessel or a digestive tract of a patient.

In the present invention, a proximal side of the catheter refers to a direction toward a user's hand with respect to the extending direction of the catheter, and a distal side refers to the opposite direction from the proximal side, that is, the direction toward a treatment target side.

The tube 32 has a flexible tubular structure, and can be made of, for example, synthetic resin such as polyolefin resins (e.g., polyethylene or polypropylene), polyamide resins (e.g., nylon), polyester resins (e.g., PET), aromatic polyetherketone resins (e.g., PEEK), polyether polyamide resins, polyurethane resins, polyimide resins and fluororesins (e.g., PTFE, PFA, ETFE), or metal such as stainless steel, carbon steel and nickel-titanium alloys. The metal material can also be used for a metal wire embedded within a synthetic resin tube. The length of the tube 32 in an axial direction (distal-proximal direction) is several times to several tens of times longer than the length of the handle 1 in the same direction, and is, for example, about 500 mm to 1200 mm. The outer diameter of the tube 32 may be, for example, approximately 0.6 mm to 5 mm.

The tube 32 has a lumen, and may have either a single lumen structure with one lumen or a multilumen structure with multiple lumens. The tube 32 may have a coaxial structure with a plurality of coaxial lumens. A wire for operating the tube 32 is disposed in the lumen of the tube 32. The wire is provided, for example, to control bending of a distal end part of tube 32. In this case, a distal end part of the wire is preferably fixed to the distal end part of the tube 32, for example to a distal one-third part of the tube 32. In the lumen of the tube 32, a conducting wire, an optical fiber, an endoscope or the like may be disposed and the tube 32 may have a lumen for inserting a guidewire or another treatment instrument, or a lumen for flowing a drug, a contrast agent or any fluid.

The handle 1 is provided on a proximal side of the tube 32, and when assembled as a catheter, a proximal end of the wire disposed in the lumen of the tube 32 is connected to the handle 1.

Details of the catheter handle is explained with reference to FIGS. 2 to 5. FIG. 2 shows a plan view of the internal structure of the catheter handle provided in the catheter shown in FIG. 1, FIG. 3 shows a plan view of the internal structure of the catheter handle shown in FIG. 2 with a slider partially cut away along an axial direction, FIG. 4 shows a plan view of the internal structure of the catheter handle shown in FIG. 2 with a slider and a shaft removed, and FIG. 5 shows a cross-sectional view taken along a line V-V of the catheter handle shown in FIG. 2. FIG. 2 shows a plan view of the catheter handle in which a handle body, which serve as a housing of the catheter handle, and a rotary knob are cut away along the axial direction so that the internal structure can be seen. In FIG. 5, the cut away portion of the handle body in FIG. 2 is shown in dotted lines.

The handle 1 according to an embodiment of the present invention comprises: a handle body 2 having an inner cavity extending in the axial direction x; a shaft 3 disposed in the inner cavity of the handle body 2, extending in the axial direction x, and fixed to the handle body 2; a slider 4 disposed on an outside of the shaft 3, having a first engagement part 21 extending spirally on an outer surface thereof, and configured so as to be displaceable in the axial direction x along the shaft 3; and a rotary knob 5 provided so as to be rotatable around the axial direction x relative to the handle body 2, and having a second engagement part 22 on an inner surface thereof, which engages with the first engagement part 21 of the slider 4. In the handle 1, the axial direction x corresponds to a direction in which a rotation axis of the rotary knob 5 extends, and a proximal side and a distal side are defined as one side and the other side with respect to the axial direction x. Further, a radial direction is defined as a direction orthogonal to the axial direction x.

The handle body 2 has an inner cavity extending in the axial direction x (see FIG. 4). The inner cavity of the handle body 2 preferably has a cylindrical portion centered on the axial direction x, and the rotary knob 5 is preferably disposed in the cylindrical portion of the inner cavity. The rotary knob 5 has a rotation axis extending in the axial direction x and is provided so as to be rotatable around the axial direction x relative to the handle body 2. The rotary knob 5 is preferably disposed in at least a part of the inner cavity of the handle body 2, and preferably only a part thereof in the axial direction x is disposed in the inner cavity of the handle body 2.

It is preferable that the rotary knob 5 has an inner cavity extending in the axial direction x and forms an inner space of the handle 1 together with the inner cavity of the handle body 2. The inner cavity of the rotary knob 5 preferably has a cylindrical portion centered on the axial direction x. It is preferable that the inner cavity of the rotary knob 5 is connected to the inner cavity of the handle body 2 in the axial direction x, the inner cavity of the rotary knob 5 and the inner cavity of the handle body 2 integrally form the inner space of the handle 1, and the shaft 3 and the slider 4 are disposed in this inner space.

It is preferable that the handle body 2 is configured such that at least one of the distal and proximal sides thereof is open, and the rotary knob 5 is inserted from the open distal or proximal side of the handle body 2, whereby the rotary knob 5 is placed in the inner cavity of the handle body 2. Meanwhile, it is preferable that the rotary knob 5 is inserted into the handle body 2 and is configured such that the proximal or distal side located in the inner cavity of the handle body 2 is open. Thereby, the inner space of the handle 1 is integrally formed by the inner cavity of the handle body 2 and the inner cavity of the rotary knob 5. In the handle 1 shown in the drawings, the distal side of the handle body 2 is open, the proximal side of the rotary knob 5 is open, and the rotary knob 5 is inserted into the inner cavity of the handle body 2 from the distal side of the handle body 2. In the handle 1, the handle body 2 and the rotary knob 5 are exposed to the outside, and the handle 1 can be operated by, for example, holding the handle body 2 with one hand and the rotary knob 5 with the other hand and rotating the rotary knob 5 against the handle body 2.

The shaft 3 is disposed in the inner cavity of the handle body 2 so as to extend in the axial direction x (see FIG. 3). The shaft 3 is fixed to the handle body 2 and is provided so as not to rotate or move relative to the handle body 2. The shaft 3 may be formed integrally with the handle body 2. The shaft 3 is preferably arranged at a position that serves as the rotation axis of the rotary knob 5. The shaft 3 is preferably provided so as to extend from the inner cavity of the handle body 2 to the inner cavity of the rotary knob 5, and may be provided so as to further extend distally and/or proximally beyond the handle body 2 and the rotary knob 5.

The tube 32 is preferably connected to a distal side of the shaft 3. A connection part between the shaft 3 and the tube 32 may be located in the inner space of the handle 1, may be located distal to the inner space of the handle 1, or may be located outside the handle 1. The shaft 3 can also be formed integrally with the tube 32.

The shaft 3 may be formed solid or hollow. It is preferable that the shaft 3 is formed hollow and a lumen of the shaft 3 communicates with the lumen of the tube 32. This allows a treatment instrument to be delivered to a treatment site or a drug or a contrast agent to be injected from the proximal side of the catheter 31 through the lumen of the shaft 3 and the lumen of the tube 32. Examples of the treatment instrument include an electrode catheter, an ablation catheter, a mapping catheter, a balloon catheter, a microcatheter, forceps, a laser probe, a fiberscope, a high-frequency treatment instrument, an electrohydraulic impact fracture probe, and others. To allow insertion of such a treatment instrument, the shaft 3 preferably has a proximal opening on the outside of the handle 1. The shaft 3 may have a branch part, and the branch part of the shaft 3 may be provided with a switching cock. This makes it possible to separately provide, for example, an insertion port for a treatment instrument and an injection port for a drag or the like.

The slider 4 is disposed on the outside of the shaft 3. The slider 4 is disposed in the inner space of the handle 1 and extends from the inner cavity of the handle body 2 to the inner cavity of the rotary knob 5 (see FIGS. 2 and 3). The slider 4 is disposed on the outside in the radial direction relative to the shaft 3, and therefore, it is preferable that the slider 4 is provided with a through hole extending in the axial direction x and passing through the slider 4 in the axial direction x, and the shaft 3 is inserted into the through hole.

The slider 4 is configured so as to be displaceable in the axial direction x along the shaft 3, that is, it is provided so as to be movable in the axial direction x in the inner space of the handle 1. Therefore, the length of the slider 4 in the axial direction x is preferably shorter than the length of the shaft 3 in the axial direction x in the inner space of the handle 1, and is preferably shorter than the length of the inner space of the handle 1 in the axial direction x.

The slider 4 is configured to be displaced in the axial direction x by rotating the rotary knob 5 around the axial direction x. To this end, a first engagement part 21 extending spirally is formed on the outer surface of the slider 4, and a second engagement part 22 which engages with the first engagement part 21 is formed on the inner surface of the rotary knob 5.

The first engagement part 21 is provided on the outer surface of the slider 4, namely, on the outer surface of the slider 4 in the radial direction, so as to extend spirally. In detail, the first engagement part 21 is provided on the outer surface of the slider 4 so as to extend in a spiral shape with the axial direction x of the handle 1 as an axis, and is preferably provided on the outer surface of the slider 4 formed in a cylindrical shape. The first engagement part 21 may be formed continuously or intermittently. The first engagement part 21 may be formed in a clockwise spiral shape or a counterclockwise spiral shape from the proximal side toward the distal side.

The second engagement part 22 is provide on the inner surface of the rotary knob 5, that is, on the inner surface of the rotary knob 5 in the radial direction, so as to be capable of engaging with the first engagement part 21 (see FIGS. 3 and 4). The second engagement part 22 is formed to extend spirally on the inner surface of the rotary knob 5, and in detail, it is formed to extend in a spiral shape with the axial direction x of the handle 1 as an axis. The second engagement part 22 is preferably provided on the inner surface of the rotary knob 5 formed in a cylindrical shape. The second engagement part 22 may be formed continuously or intermittently.

Since the first engagement part 21 is provided on the outer surface of the slider 4 and the second engagement part 22 is provided on the inner surface of the rotary knob 5 as described above, the slider 4 can be moved in the axial direction x in the inner space of the handle 1 by rotating the rotary knob 5 around the axial direction x. That is, the first engagement part 21 and the second engagement part 22 formed in a spiral shape makes it possible to convert rotational movement of the rotary knob 5 around the axial direction x into parallel movement of the slider 4 in the axial direction x.

The first engagement part 21 and the second engagement part 22 may be formed to extend continuously or intermittently in a spiral shape for one or more rounds, or may be formed to extend for less than one round. It is preferable that at least one of the first engagement part 21 and the second engagement part 22 is formed so as to extend continuously or intermittently in a spiral shape for one or more rounds, more preferably formed so as to extend for two or more rounds, and even more preferably formed so as to extend for three or more rounds. Meanwhile, the other of the first engagement part 21 and the second engagement part 22 may be formed continuously or intermittently in a spiral shape so as to extend less than one round, and may be formed, for example, so as to extend only half a round in a spiral shape. In the handle 1 shown in the drawings, the first engagement part 21 provided on the slider 4 is formed to extend spirally for one or more rounds, and the second engagement part 22 provided on the rotary knob 5 is formed to extend spirally for less than one round.

The first engagement part 21 and the second engagement part 22 can be formed by a combination of a convex part and a groove. That is, it is preferable that one of the first engagement part 21 and the second engagement part 22 is a convex part and the other of them is a groove. In the case where the first engagement part 21 or the second engagement part 22 is formed as a groove, the groove is preferably formed to extend continuously in a spiral shape. The groove may be a bottomed groove or a through groove, and in view of ensuring the strength of the slider 4 or the rotary knob 5, the groove is preferably a bottomed groove. Meanwhile, in the case where the first engagement part 21 or the second engagement part 22 is formed as a convex part, the convex part may be provided in a continuously extending spiral shape or in an intermittently extending spiral shape. In the drawing, the first engagement part 21 provided on the slider 4 is formed as a convex part (a convex strip), and the second engagement part 22 provided on the rotary knob 5 is formed as a groove.

In the inner cavity of the handle 1, a linear member 6 which is bent on the proximal side and the ends of which extend toward the distal side is provided (see FIG. 3). Both ends of the linear member 6 that extend toward the distal side are disposed in the lumen of the tube 32. To explain this in detail, the linear member 6 has a first end as one end and a second end as the other end, and a portion including the first end is defined as a first portion 6A, a portion including the second end is defined as a second portion 6B, and a portion between the first portion 6A and the second portion 6B is defined as an intermediate portion 6C. The first end and the second end are defined as one end and the other end when the linear member 6 is extended straight. The linear member 6 is bent at the intermediate portion 6C, and at least a part of the intermediate portion 6C including the bent part is disposed in the inner cavity of the handle body 2, and at least a part of the first portion 6A and the second portion 6B are disposed in the lumen of tube 32.

The first portion 6A and second portion 6B of the linear member 6 serve as wires for controlling the tube 32. A distal end part of the first portion 6A, that is, the first end and the vicinity thereof, and a distal end part of the second portion 6B, that is, the second end and the vicinity thereof, are preferably fixed to the distal end part of the tube 32. In this case, in operating the handle 1, the distal end part of the tube 32 can be bent to one side by pulling the first portion 6A proximally, and the distal end part of the tube 32 can be bent to another side by pulling the second portion 6B proximally. The distal end part of the first portion 6A can be defined, for example, as a portion within 100 mm proximally from the first end of the first portion 6A, and the distal end part of the second portion 6B can be defined, for example, as a portion within 100 mm from the second end of the second portion 6B. The distal end part of the tube 32 can be defined, for example, as a portion within 100 mm proximally from the distal end of the tube 32.

It is preferable that the linear member 6 extends outward from the lumen of the shaft 3 or the tube 32 in the inner space of the handle 1, and the intermediate portion 6C of the linear member 6 extends from the inner cavity of the rotary knob 5 to the inner cavity of the handle body 2. More preferably, the linear member 6 extends outward from the lumen of the shaft 3 or the tube 32 in the inner space of the handle 1 at a position distal to the distal end of the slider 4 in the state where the slider 4 is displaced to a most distal side.

It is preferable that the linear member 6 is disposed in an interior of the slider 4, that is, in the through hole extending in the axial direction x, at a portion overlapping with the slider 4 in the axial direction x. For example, a gap extending in the axial direction x (a gap passing through the slider 4 in the axial direction x) is formed between the inner surface of the through hole of the slider 4 and the shaft 3, and the linear member 6 is preferable disposed in the gap.

A return guide 9 for guiding the bending of the intermediate portion 6C of the linear member 6 is provided in the inner cavity of the handle body 2, and at least a part of the intermediate portion 6C of the linear member 6 is in contact with the return guide 9. The return guide 9 is fixed to the handle body 2 and is provided so as not to rotate or move relative to the handle body 2. The return guide 9 may be formed integrally with the handle body 2. Alternatively, the return guide 9 may be configured to be fixable to the handle body 2 at different positions in the axial direction x. In FIG. 3, the return guide 9 is fixed to the handle body 2 with screws.

Preferably, the return guide 9 is provided at a position overlapping with the slider 4 in the axial direction x or provided proximal to the slider 4. More preferably, the return guide 9 is provided proximal to the slider 4 in the state where the slider 4 is displaced to a most proximal side.

The return guide 9 is provided with a guide passage for making a U-turn of the linear member 6 toward the distal side, and the linear member 6 is in contact with the guide passage. The guide passage is preferably formed in a U-shape or an arc shape (for example, semicircular shape) that is convex toward the proximal side in a plan view along the axial direction x. The guide passage is preferably formed as a tubular passage, and the intermediate portion 6C of the linear member 6 is preferably inserted into the lumen of the tubular passage.

In the inner space of the handle 1, the linear member 6 is formed to be displaceable in the axial direction x in conjunction with a portion on the first end side (the first portion 6A side) from the return guide 9 and a portion on the second end side (the second portion 6B side) from the return guide 9. In the linear member 6, the portion on the first end side from the return guide 9 is connected to the portion on the second end side from the return guide 9 via a part in contact with the return guide 9, and therefore, when the portion on the first end side from the return guide 9 is displaced proximally, the portion on the second end side from the return guide 9 can be displaced distally, and when the portion on the first end side from the return guide 9 is displaced distally, the portion on the second end side from the return guide 9 can be displaced proximally.

The entirety of the first portion 6A and the second portion 6B may be disposed in the tube 32, or only a part thereof may be disposed in the tube 32. The entirety of the intermediate portion 6C may be disposed in the inner space of the handle 1, or only a part thereof may be disposed in the inner space of the handle 1. In FIG. 3, the intermediate portion 6C is connected to the first portion 6A at a first connecting part 7 and is connected to the second portion 6B at a second connecting part 8 in the inner space of the handle 1. In this manner, the first portion 6A and the second portion 6B preferably extend from the tube 32 to the inner space of the handle 1, specifically, to the inner cavity of the rotary knob 5, and a part of the first portion 6A and the second portion 6B is preferably placed in the inner cavity of the rotary knob 5, irrespective of the displacement of the linear member 6. The first portion 6A and the second portion 6B may extend to the inner cavity of the handle body 2.

The intermediate portion 6C is disposed in the inner cavity of the handle body 2 in contact with the return guide 9. The intermediate portion 6C is preferably arranged to be bent toward the proximal side in the inner cavity of the handle body 2. It is preferable that the intermediate portion 6C includes the entire portion of the linear member 6 that comes into contact with the return guide 9 when the linear member 6 is displaced in the axial direction x. In other words, in the linear member 6, it is preferably the intermediate portion 6C that comes into contact with the return guide 9. Furthermore, it is preferable that a part of the intermediate portion 6C is located in the inner cavity of the rotary knob 5, irrespective of the displacement of the linear member 6 in the axial direction x.

The linear member 6 is fixed to the slider 4 at a part of the linear member 6 on the first end side from the contacting part of the linear member 6 with the return guide 9. In FIG. 3, the linear member 6 is fixed to the slider 4 with a fixture 10 mounted on the slider 4. As a result, when rotating the rotary knob 5 around the axial direction x, the slider 4 is moved in the axial direction x, and accordingly, the portion of the linear member 6 on the first end side from the return guide 9 can be displaced in the axial direction x and the portion of the linear member 6 on the second end side from the return guide 9 can be displaced in the opposite axial direction x. Specifically, when the slider 4 is moved proximally, the portion of the linear member 6 on the first end side from the return guide 9 is displaced proximally and the portion of the linear member 6 on the second end side from the return guide 9 is displaced distally, accordingly. When the slider 4 is moved distally, the portion of the linear member 6 on the first end side from the return guide 9 is displaced distally and the portion of the linear member 6 on the second end side from the return guide 9 is displaced proximally, accordingly. Thereby, the first portion 6A and the second portion 6B of the linear member 6 disposed in the lumen of the tube 32 can be pulled proximally or pushed distally, which makes it possible to, for example, control the bending of the distal end part of the tube 32. For example, by rotating the rotary knob 5 clockwise viewed from the proximal side, the distal end part of the tube 32 can be bent in one direction, and by rotating the rotary knob 5 counterclockwise viewed from the proximal side, the distal end part of the tube 32 can be bent in another direction.

The linear member 6 is preferably fixed to the inner surface of the slider 4. In FIG. 3, the fixture 10 for the linear member 6 is provide on the inner surface of the slider 4, and the linear member 6 is fixed to the fixture 10; however, the linear member 6 may be directly fixed to the inner surface of the slider 4 with an adhesive or the like. In the case where the linear member 6 is directly fixed to the inner surface of the slider 4, the fixture 10 may not be provided. Examples of methods for fixing the linear member 6 to the fixture 10 or to the inner surface of the slider 4 include bonding with an adhesive, welding, fitting, caulking, screwing, and others.

Although not shown in the drawings, the slider 4 may have an inner layer and an outer layer, and the linear member 6 may be disposed between the inner layer and the outer layer. In this case, the linear member 6 comes to be fixed to the slider 4 by being sandwiched between the inner layer and the outer layer.

It is preferable that the fixed part of the linear member 6 to the slider 4 is positioned proximal to the point where the linear member 6 extends outward from the lumen of the shaft 3 or the tube 32 in the state where the slider 4 is located at the most distal side. In other words, it is preferable that the linear member 6 extends outward from the lumen of the shaft 3 or the tube 32 at a position distal to the fixed part to the slider 4 in the state where the slider 4 is located at the most distal side.

At a part of the linear member 6 on the first end side from the contacting part of the linear member 6 with the return guide 9 in the state where the slider 4 is located at the most proximal side, the linear member 6 is fixed to the slider 4. By fixing the linear member 6 to the slider 4 in this manner, the linear member 6 comes to be fixed to the slider 4 at the part of the linear member 6 on the first end side from the contacting part of the linear member 6 with the return guide 9, irrespective of the displacement of the slider 4 in the axial direction x. On the other hand, it is preferable that the linear member 6 is not fixed to the slider 4 at a part of the linear member 6 on the second end side from the contacting part of the linear member 6 with the return guide 9, and in particular, it is preferable that, at the part of the linear member 6 on the second end side from the contacting part of the linear member 6 with the return guide 9 in the state where the slider 4 is located at the most proximal side, the linear member 6 is not fixed to the slider 4.

For the linear member 6, a metal wire such as stainless steel, carbon steel, and nickel-titanium alloy, or a resin wire (i.e., fiber material) made of synthetic resin such as polyamide resin (e.g., nylon), polyolefin resin (e.g., polyethylene and polypropylene), polyester resin (e.g., PET), aromatic polyamide resin (e.g., aramid), and fluororesin (e.g., PTFE, PFA, FEP, ETFE) can be used. These metal and resin wires may have a monofilament structure or a multifilament structure. The linear member 6 may be covered with a tubular body formed of coiled metal or synthetic resin.

The first portion 6A, the second portion 6B, and the intermediate portion 6C of the linear member 6 may be made of the same material or may be made of different materials from each other. It is preferable that the intermediate portion 6C is made of a material different from the first portion 6A and the second portion 6B. The intermediate portion 6C is preferably made of an easily bendable material so that it can be bent at the return guide 9 with a relatively small bending radius. Meanwhile, the first portion 6A and the second portion 6B are disposed in the lumen of the tube 32, and are required to ensure that the movement of the linear member 6 in the axial direction x on the handle 1 side is suitably transmitted via the first portion 6A and the second portion 6B to the distal end part of the tube 32, and thus, the first portion 6A and the second portion 6B are preferably made of a relatively rigid material, and are not required to have more flexibility than the intermediate portion 6C. Therefore, it is preferable that the intermediate portion 6C has lower bending rigidity than the first portion 6A and the second portion 6B.

The bending rigidity of the first portion 6A, the second portion 6B, and the intermediate portion 6C can be measured, for example, according to the bending resistance test of JIS L 1913:2010, and the magnitude of the bending rigidity can be compared from the results. Alternatively, the bending rigidity can be measured by using a bending tester such as a single bending tester KES-FB2-SH or a pure bending tester KES-FB2-S manufactured by Kato Tech Co., Ltd. and the magnitude can be compared therefrom.

It is also preferable that the first portion 6A and the second portion 6B have higher axial rigidity than the intermediate portion 6C. For example, it is preferable that the intermediate portion 6C is composed a resin wire, and the first portion 6A and the second portion 6B are composed of a metal wire.

The intermediate portion 6C of the linear member 6 is preferably composed of a rope. This makes it easier to bend the intermediate portion 6C smoothly at the return guide 9 while ensuring the strength of the intermediate portion 6C. The rope may be a fiber rope made of a fiber material or a wire rope made of a metal material, and is preferably a fiber rope. Thereby, the intermediate portion 6C can be easily bent smoothly at the return guide 9 while the strength of the intermediate portion 6C is ensured. The fiber rope is formed by twisting twisted yarns together to form strands, which are further twisted together, and so on. As a result, the fiber rope has large irregularities formed on its surface by twisting, whereby the contact area with the return guide 9 can be reduced, and slipperiness at the return guide 9 can be improved. In addition, it becomes easier to ensure the rigidity of the intermediate portion 6C in the axial direction x, and flexing of the intermediate portion 6C can be suppressed.

The fiber rope is preferably made of a high-strength fiber material to prevent breakage, and is preferably made of so-called super fiber. Examples of the super fiber include aramid fibers, ultrahigh molecular weight polyethylene fibers, polyarylate fibers, ultrahigh strength polyvinyl alcohol fibers, polyparaphenylenebenzobisoxazole (PBO) fibers, polyphenylene sulfide (PPS) fibers, and others. The super fiber preferably has, for example, a tensile strength of 1 GPa or more, preferably 2 GPa or more, and an elastic modulus of 25 GPa or more, preferably 50 GPa or more.

The first portion 6A and the second portion 6B of the linear member 6 are preferably composed of a metal wire. This facilitates responsive control of bending or the like of the distal end part of the tube 32 by pulling proximally or pushing distally the first portion 6A and the second portion 6B disposed in the lumen of the tube 32. The first portion 6A and the second portion 6B may be a wire rope made of a metal.

The outer diameter of the linear member 6 can be, for example, about 100 μm to 1500 μm. The outer diameter referred to here means a diameter when the cross-sectional shape is circular, and represents an average value of the major axis and the minor axis when the cross-sectional shape is non-circular. The major axis means the length of the cross-sectional shape in the major axis direction (maximum diameter of the cross-sectional shape), and the minor axis means the longest of the lengths in the minor axis direction, which is perpendicular to the major axis direction.

It is preferable that the outer diameter of the intermediate portion 6C is larger than the outer diameter of the first portion 6A and the outer diameter of the second portion 6B. By making the outer diameter of the intermediate portion 6C to be large to a certain extent, the intermediate portion 6C is less likely to be caught or hitched by the slider 4 or the rotary knob 5 when the slider 4 is moved in the axial direction x.

In the case where the intermediate portion 6C is made of a material different from the first portion 6A and the second portion 6B, joining of the intermediate portion 6C with the first portion 6A at the first connecting part 7 and joining of the intermediate portion 6C with the second portion 6B at the second connecting part 8 can be carried out by bonding, welding, caulking, tying or the like.

In order to prevent the slider 4 from rotating together with the rotary knob 5 when rotating the rotary knob 5 around the axial direction x, the handle 1 is preferably configured such that the slider 4 has a third engagement part 23 on the outer surface of the slider 4, the handle body 2 has a fourth engagement part 24 on the inner surface of the handle body 2, which engages with the third engagement part 23, and at least one of the third engagement part 23 and the fourth engagement part 24 is provided so as to extend in the axial direction x. Thereby, the slider 4 can be moved along the axial direction x without the slider 4 rotating around the axial direction x.

The third engagement part 23 and the fourth engagement part 24 can be formed by a combination of a convex part and a groove. That is, it is preferable that one of the third engagement part 23 and the fourth engagement part 24 is a convex part and the other of them is a groove. In the handle 1 shown in the drawings, the third engagement part 23 provided on the outer surface of the slider 4 is formed as a convex part, and the fourth engagement part 24 provided on the inner surface of the handle body 2 is formed as a groove.

The third engagement part 23 or the fourth engagement part 24 formed as a groove is preferably formed to extend in the axial direction x, and more preferably formed to extend continuously in the axial direction x. The groove may be a bottomed groove or a through groove, and in view of ensuring the strength of the slider 4 or the handle body 2, the groove is preferably a bottomed groove. Meanwhile, the third engagement part 23 or the fourth engagement part 24 formed as a convex part may be or may not be formed to extend in the axial direction x.

As shown in the drawings, in the case where the third engagement part 23 is formed as a convex part and the fourth engagement part 24 is formed as a groove, the convex part formed as the third engagement part 23 on the outer surface of the slider 4 is preferably located proximal to the first engagement part 21 in the slider 4. At least a part of the groove formed as the fourth engagement part 24 on the inner surface of the handle body 2 is preferably located distal to the return guide 9.

Although not shown in the drawings, in the case where a groove is formed as the third engagement part 23 on the outer surface of the slider 4, the groove may be located so as to overlap with the first engagement part 21 in the axial direction x in the slider 4 or may be located proximal to the first engagement part 21 in the slider 4. In this case, at least a part of a convex part formed as the fourth engagement part 24 on the inner surface of the handle body 2 is preferably located distal to the return guide 9.

In order to prevent the slider 4 from rotating together with the rotary knob 5 when rotating the rotary knob 5 around the axial direction x, the handle 1 may be configured such that the slider 4 has a fifth engagement part 25 on the inner surface of the slider 4, the shaft 3 has a sixth engagement part 26 on the outer surface of the shaft 3, which engages with the fifth engagement part 25, and at least one of the fifth engagement part 25 and the sixth engagement part 26 is provided so as to extend in the axial direction x, as shown in FIG. 5. Even in the case where the fifth engagement part 25 and the sixth engagement part 26 are provided in this manner, the slider 4 can be moved along the axial direction x without the slider 4 rotating around the axial direction x.

The fifth engagement part 25 and the sixth engagement part 26 can be formed by a combination of a convex part and a groove. That is, it is preferable that one of the fifth engagement part 25 and the sixth engagement part 26 is a convex part and the other of them is a groove. In FIG. 5, the fifth engagement part 25 provided on the inner surface of the slider 4 is formed as a groove, and the sixth engagement part 26 provided on the outer surface of the shaft 3 is formed as a convex part.

The fifth engagement part 25 or the sixth engagement part 26 formed as a groove is preferably formed to extend in the axial direction x, and more preferably formed to extend continuously in the axial direction x. The groove may be a bottomed groove or a through groove, and in view of ensuring the strength of the slider 4 or the shaft 3, the groove is preferably a bottomed groove. Meanwhile, the fifth engagement part 25 or the sixth engagement part 26 formed as a convex part may be or may not be formed to extend in the axial direction x.

As shown in FIG. 5, in the case where the fifth engagement part 25 is formed as a groove and the sixth engagement part 26 is formed as a convex part, the groove formed as the fifth engagement part 25 on the inner surface of the slider 4 may be located so as to overlap with the first engagement part 21 in the axial direction x in the slider 4 or may be located proximal or distal to the first engagement part 21 in the slider 4. At least a part of the convex part formed as the sixth engagement part 26 on the outer surface of the shaft 3 is preferably located distal to the return guide 9.

Although not shown in the drawings, in the case where a convex part is formed as the fifth engagement part 25 on the inner surface of the slider 4, the convex part may be located so as to overlap with the first engagement part 21 in the axial direction x in the slider 4 or may be located proximal or distal to the first engagement part 21 in the slider 4. In this case, at least a part of a groove formed as the sixth engagement part 26 on the outer surface of the shaft 3 is preferably located distal to the return guide 9.

In the case where the third engagement part 23 and the fourth engagement part 24 are provided in the handle 1, the fifth engagement part 25 and the sixth engagement part 26 may not be provided. Conversely, in the case where the fifth engagement part 25 and the sixth engagement part 26 are provided in the handle 1, the third engagement part 23 and the fourth engagement part 24 may not be provided. In either case, when rotating the rotary knob 5 around the axial direction x, the slider 4 can be moved along the axial direction x without the slider 4 rotating around the axial direction x. Of course, the handle 1 may be provided with the third engagement part 23 and the fourth engagement part 24, and further provided with the fifth engagement part 25 and the sixth engagement part 26.

Next, another configuration example of the handle 1, specifically, a preferred embodiment of the first connecting part 7 and the second connecting part 8 in the linear member 6 is explained. FIGS. 6 to 9 show another configuration example of the internal structure of the handle 1 provided in the catheter 31 shown in FIG. 1. FIG. 6 shows a plan view of another embodiment of the internal structure of the catheter handle, FIG. 7 shows a plan view of the internal structure of the catheter handle shown in FIG. 6 with the slider partially cut away along the axial direction, FIG. 8 shows a plan view of the catheter handle shown in FIG. 6 in the state where the slider displaced to the most distal side, and FIG. 9 shows a plan view of the catheter handle shown in FIG. 6 in the state where the slider displaced to the most proximal side. In the explanation of the catheter handle shown in FIGS. 6 to 9, descriptions which overlap with the above description are omitted.

In the handle 1 shown in FIGS. 6 to 9, the linear member 6 is configured such that the first connecting part 7 in which the intermediate portion 6C is connected to the first portion 6A and the second connecting part 8 in which the intermediate portion 6C is connected to the second portion 6B are located distal to the slider 4, irrespective of the displacement of the slider 4 in the axial direction X. Specifically, the linear member 6 is configured such that a proximal part of the first portion 6A is connected to the intermediate portion 6C at the first connecting part 7, a proximal part of the second portion 6B is connected to the intermediate portion 6C at the second connecting part 8, and the first connecting part 7 and the second connecting part 8 are located distal to the distal end of the slider 4 in the state where the slider 4 is displaced to the most distal side (see FIG. 8). By forming the first connecting part 7 and the second connecting part 8 in such a position, the first portion 6A and the second portion 6B can be positioned distal to the distal end of the slider 4, irrespective of the displacement of the slider 4 in the axial direction x. Therefore, when the slider 4 is moved in the axial direction x, the first portion 6A and the second portion 6B are prevented from coming into contact with the slider 4. As a result, the slider 4 can be smoothly moved in the axial direction x, and the generation of abnormal noise due to the slider 4 coming into contact with the first portion 6A or the second portion 6B can be suppressed.

FIG. 8 shows the handle 1 with the slider 4 displaced to the most distal side, FIG. 9 shows the handle 1 with the slider 4 displaced to the most proximal side, and FIG. 6 shows the handle 1 with the slider 4 positioned approximately in the middle in the axial direction x. Since the intermediate portion 6C is fixed to the slider 4 on the first end side from the contacting part with the return guide 9, the length between the first connecting part 7 and the distal end of the slider 4 in the axis direction x is not changed when the slider 4 is displaced in the axial direction x. Therefore, by fixing the intermediate portion 6C to the slider 4 so that the first connecting part 7 is positioned distal to the distal end of the slider 4, the first connecting part 7 can be located distal to the distal end of the slider 4 irrespective of the displacement of the slider 4 in the axial direction x. Meanwhile, the relative position of the second connecting part 8 to the slider 4 in the axial direction x changes depending on the displacement of the slider 4 in the axial direction x, and when the slider 4 is displaced to the most distal side, the second connecting part 8 is located on the most proximal side. Therefore, by positioning the second connecting part 8 distal to the distal end of the slider 4 in the state where the slider 4 is displaced to the most distal side, the second connecting part 8 can be located distal to the distal end of the slider 4, irrespective of the displacement of the slider 4 in the axial direction x.

It is preferable that at least a part of the first connecting part 7 and the second connecting part 8 is located distal to the distal end of the slider 4 in the state where the slider 4 is displaced to the most distal side, and is more preferable that the entirety of the connecting part 7 and the entirety of the second connecting part 8 are located distal to the distal end of the slider 4 in the state where the slider 4 is displaced to the most distal side. Furthermore, it is preferable that the entirety of the first portion 6A and the entirety of the second portion 6B are located distal to the distal end of the slider 4 in the state where the slider 4 is displaced to the most distal side.

FIG. 10 shows an example of the configuration of the first connecting part 7 and the second connecting part 8. As shown in FIG. 10, it is preferable that a proximal end of the first portion 6A has a first annular part 11 formed in an annular shape, and an end part of the intermediate portion 6C on the first portion 6A side is tied to the first annular part 11, thereby forming the first connecting part 7, and a proximal end of the second portion 6B has a second annular part 12 formed in an annular shape, and an end part of the intermediate portion 6C on the second portion 6B side is tied to the second annular part 12, thereby forming the second connecting part 8. Thereby, the first connecting part 7 and the second connecting part 8 are formed as knots 13 of the intermediate portion 6C, and the knots 13 form the first connecting part 7 and the second connecting part 8 with a certain size. As a result, the first connecting part 7 and the second connecting part 8 are less likely to enter the gap between the inner surface of the slider 4 and the shaft 3, and the first portion 6A and the second portion 6B are prevented from coming into contact with the slider 4 even if the intermediate portion 6C flexes when the slider 4 is moved in the axial direction x. In addition, the first connecting part 7 and the second connecting part 8 can serve as a cushion, and even if the first connecting part 7 and the second connecting part 8 come into contact with the slider 4, the generation of abnormal noise is further suppressed. At least of a part of the knot 13 may be located distal to the distal end of the slider 4 in the state where the slider 4 is displaced to the most distal side, and preferably, the entirety of the knot 13 is located distal to the distal end of the slider 4 in the state where the slider 4 is displaced to the most distal side.

The first annular part 11 is preferably formed by forming the proximal end of the first portion 6A into an annular shape. The second annular part 12 is preferably formed by forming the proximal end of the second portion 6B into an annular shape. As shown in FIG. 10, the first annular part 11 can be formed by bending the proximal end of the first portion 6A to form in an annular shape and joining the first portions 6A together, and the second annular part 12 can be formed by bending the proximal end of the second portion 6B to form in an annular shape and joining the second portions 6B together. By forming the first annular part 11 and the second annular part 12 in this manner, the first annular part 11 is formed integrally with the first portion 6A and the second annular part 12 is formed integrally with the second portion 6B, which makes it easier to form the first annular part 11 and the second annular part 12 strongly.

The joining of the first portions 6A together and the joining of the second portions 6B together can be carried out by known joining means such as bonding, welding, soldering, caulking, and tying. Among these, the joining is preferably carried out by soldering, caulking, or a combination thereof, since the first portions 6A and the second portions 6B can be firmly joined together. The first annular part 11 and the second annular part 12 may be formed by attaching an annular member to the proximal end of the first portion 6A or the proximal end of the second portion 6B.

Various types of knots can be employed for tying the intermediate portion 6C to the first annular part 11 or the second annular part 12, and the types thereof are not particularly limited. Examples of the types of the knot include single knot, double knot, bowline knot, rolled knot, figure-of-eight knot, S-shaped knot, fisherman's knot, vertical knot, drawn knot, and others.

It is preferable that the knot 13 formed by tying the end part of the intermediate portion 6C on the first portion 6A side to the first annular part 11 and the knot 13 formed by tying the end part of the intermediate portion 6C on the second portion 6B side to the second annular part 12 are hardened with an adhesive or melt-solidified. As a result, the knot 13 of the intermediate portion 6C at the first connecting part 7 and the knot 13 of the intermediate portion 6C at the second connecting part 8 become difficult to be untied, and the intermediate portion 6C can be firmly connected to the first portion 6A and the second portion 6B.

It is more preferable that the knot 13 is hardened with an adhesive. That is, it is preferable that the knot 13 is hardened by applying an adhesive to the knot 13 and solidifying the adhesive. Thereby, it becomes easy to harden the knot 13 of the intermediate portion 6C, regardless of the material of the intermediate portion 6C.

The position at which the intermediate portion 6C is fixed to the slider 4 (or an installation position of the fixture 10 if the fixture 10 is provided) is not particularly limited, and the intermediate portion 6C is preferably fixed to the slider 4 at least at a distal half part of the slider 4, more preferably at least a distal one-third part of the slider 4. When the intermediate portion 6C is fixed to the slider 4 in such a position, the length from the fixed point of the intermediate portion 6C to the slider 4 to the first connecting part 7 (namely, the end of the intermediate portion 6C on the first portion 6A side) can be shortened. Therefore, when the slider 4 is displaced distally, the intermediate portion 6C is less likely to flex in a part distal to the distal end of the slider 4, and it is less likely occur that the first portion 6A comes into contact with the slider 4.

It is also preferable that the intermediate portion 6C is fixed to the slider 4 at least at a proximal one-third part of the slider 4. When the intermediate portion 6C is fixed to the slider 4 in such a position, the length from the fixed point of the intermediate portion 6C to the slider 4 to the return guide 9 can be shortened. Therefore, when the slider 4 is displaced proximally, the intermediate portion 6C is less likely to flex between the fixed point of the intermediate portion 6C to the slider 4 and the return guide 9, which makes it easier to smoothly introduce the intermediate portion 6C into the return guide 9. The intermediate portion 6C may be fixed to the slider 4 at least at the distal one-third part and the proximal one-third part of the slider 4.

In the handle 1, even if the intermediate portion 6C flexes between the fixed point of the intermediate portion 6C to the slider 4 and the second connecting part 8 (namely, the end of the intermediate portion 6C on the second portion 6B side) when moving the slider 4 proximally, the distal end part of the tube 32 is bent to one side, which pulls the second portion 6B distally, thereby making it possible to eliminate the flexing of the intermediate portion 6C. That is, when the slider 4 is displaced proximally, the first portion 6A is pulled proximally, thereby bending the distal end part of the tube 32 to one side, and accordingly, the second portion 6B is drawn into the lumen of the tube 32 and pulled distally. As a result, even if the intermediate portion 6C flexes between the fixed point to the slider 4 and the second connecting part 8, the flexing is eliminated. Similarly, even if the intermediate portion 6C flexes between the fixed point of the intermediate portion 6C to the slider 4 and the first connecting part 7 when moving the slider 4 distally, the distal end part of the tube 32 is bent to the other side, which pulls the first portion 6A distally, thereby making it possible to eliminate the flexing of the intermediate portion 6C. That is, when the slider 4 is displaced distally, the second portion 6B is pulled proximally, thereby bending the distal end part of the tube 32 to the other side, and accordingly, the first portion 6A is drawn into the lumen of the tube 32 and pulled distally. As a result, even if the intermediate portion 6C flexes between the fixed point to the slider 4 and the first connecting part 7, the flexing is eliminated.

Still another configuration example of the handle 1, specifically, another configuration example of the return guide 9 is explained, with reference to FIGS. 11 to 15. FIGS. 11 to 15 show other configuration examples of the internal structure of the handle 1 provided in the catheter 31 shown in FIG. 1. FIG. 11 shows a plan view of another embodiment of the internal structure of the catheter handle, FIG. 12 shows an enlarged plan view around the return guide of the catheter handle shown in FIG. 11, FIG. 13 shows a cross-sectional view taken along a line XIII-XIII around the return guide shown in FIG. 12, FIG. 14 shows an enlarged plan view of a modified example around the return guide shown in FIG. 11, and FIG. 15 shows a cross-sectional view taken along a line XV-XV around the return guide shown in FIG. 14. In the explanation of the catheter handle shown in FIGS. 11 to 15, descriptions which overlap with the above description are omitted.

When assembling the handle 1, it is desirable that the linear member 6 is installed in the interior of the handle 1 in an extended state with as little slack as possible, while the linear member 6 being bent proximally and in contact with the return guide 9. As a result, when the slider 4 is displaced in the axial direction x, the linear member 6 can easily displaced in the axial direction x with good response.

Specifically, the portion of the linear member 6 on the first end side (the first portion 6A side) from the return guide 9 and the portion of the linear member 6 on the second end side (the second portion 6B side) from the return guide 9 can easily be responsively displaced in the axial direction x in opposite directions to each other, in conjunction with the movement of the slider 4. As a result, the tube 32 provided on the distal side of the handle 1 can be operated with good responsive.

To facilitate the installation of the linear member 6 as described above, in the handle 1 shown in FIGS. 11 to 15, the return guide 9 is configured to be fixable to the handle body 2 at different positions in the axial direction x. The different positions in the axial direction x mean a plurality of mutually different positions in the axial direction x. By configuring the return guide 9 in this manner, it is easier to fix the return guide 9 with the linear member 6 extended when assembling the handle 1. That is, the return guide 9 can be fixed with the linear member 6 extended by placing the linear member 6 in the interior of the handle 1 with the linear member 6 being bent proximally and in contact with the return guide 9, and then adjusting the position of the return guide 9 in the axial direction x. In addition, the fixed position of the return guide 9 in the axial direction x is adjustable, and the tension of the linear member 6 can be adjusted thereby, and therefore, the linear member 6 extends in the inner cavity of the handle body 2 at approximately the same angle with respect to the axial direction x, regardless of the fixed position in the direction x. As a result, regardless of the fixed position of the return guide 9 in the axial direction x, the linear member 6 is easily introduced smoothly without being caught by the return guide 9 when the slider 4 is displaced in the axial direction x.

For making the return guide 9 to be fixable to the handle body 2 at different positions in the axial direction x, the return guide 9 and the handle body 2 are preferably configured, for example, as follows. That is, as shown in FIGS. 12 and 13, it is preferable that an elongated hole 16 extending in the axial direction x is formed in the return guide 9, and a fixture 18 for fixing the return guide 9 is inserted through the elongated hole 16 and is fitted or screwed into the handle body 2. FIG. 12 shows a plan view of the return guide 9 and the inner surface of the handle body 2 inside the handle 1, and FIG. 13 shows a cross-sectional view taken along a line XIII-XIII in FIG. 12. In FIGS. 12 and 13, a screw is used as the fixture 18, and the fixture 18 is screwed into the handle body 2.

The fixture 18 is inserted through the elongated hole 16 of the return guide 9, and the return guide 9 is pressed against the handle body 2 by the fixture 18, thereby fixing the return guide 9 to the handle body 2. By loosening the fixture 18, the return guide 9 can be moved in the axial direction x within the range where the fixture 18 is present in the elongated hole 16. The fixture 18 may be a pin, and in this case, the fixture 18 is fitted into the handle body 2.

It is preferable that a seventh engagement part 27 is provided on the inner surface of the handle body 2, an eighth engagement part 28, which engages with the seventh engagement part 27, is provided on the return guide 9, and at least one of the seventh engagement part 27 and the eighth engagement parts 28 is provided in a plurality arranged in the axial direction x. By providing the seventh engagement part 27 and the eighth engagement part 28 on the handle body 2 and the return guide 9, respectively, the return guide 9 can be stably fixed to the handle body 2 at different positions in the axial direction x.

In FIGS. 12 and 13, a plurality of the seventh engagement parts 27 are provided on the inner surface of the handle body 2 arranged in the axial direction x. The seventh engagement part 27 of the handle body 2 is formed as a concave part, and the eighth engagement part 28 of the return guide 9 is formed as a convex part. By engaging the convex part of the eighth engagement part 28 with the concave part of the seventh engagement part 27, the return guide 9 can be stably fixed to the handle body 2 at different positions in the axial direction x. The seventh engagement part 27 may be formed as a convex part, and the eighth engagement part 28 may be formed as a concave part.

To making the return guide 9 to be fixed to the handle body 2 at different positions in the axial direction x, the return guide 9 and the handle body 2 may be configured as shown in FIGS. 14 and 15, for example. That is, an elongated hole 17 extending in the axial direction x may be formed in the handle body 2, and a fixture 18 for fixing the return guide 9 may be inserted through the elongated hole 17 and be fitted or screwed into the return guide 9. FIG. 14 shows a plan view of the return guide 9 and the inner surface of the handle body 2 inside the handle 1, and FIG. 15 shows a cross-sectional view taken along a line XV-XV in FIG. 14. In FIGS. 14 and 15, a screw is used as the fixture 18, and the fixture 18 is screwed into the return guide 9.

The fixture 18 is inserted through the elongated hole 17 of the handle body 2, and the return guide 9 is pressed against the handle body 2 by the fixture 18, thereby fixing the return guide 9 to the handle body 2. By loosening the fixture 18, the return guide 9 can be moved in the axial direction x within the range where the fixture 18 is present in the elongated hole 17. The fixture 18 may be a pin, and in this case, the fixture 18 is fitted into the return guide 9.

In FIGS. 14 and 15, it is also preferable that a seventh engagement part 27 is provided on the inner surface of the handle body 2, an eighth engagement part 28, which engages with the seventh engagement part 27, is provided on the return guide 9, and at least one of the seventh engagement part 27 and the eighth engagement parts 28 is provided in a plurality arranged in the axial direction x. By providing the seventh engagement part 27 and the eighth engagement part 28 on the handle body 2 and the return guide 9, respectively, the return guide 9 can be stably fixed to the handle body 2 at different positions in the axial direction x. As explained above, the seventh engagement part 27 and the eighth engagement part 28 can be formed by a combination of a concave part and a convex part.

As shown in FIGS. 12 to 15, it is preferable that the return guide 9 comprises a guiding tube 14 through which the intermediate portion 6C of the linear member 6 is inserted, and a holding member 15 which holds the guiding tube 14. The guiding tube 14 is arranged in a shape convex toward the proximal side (for example, U-shaped, arcuate, semicircular), and the holding member 15 is provided for the guiding tube 14 to be held in such a shape. The holding member 15 is preferably configured to be fixable to the handle body 2 at different positions in the axial direction x. In this case, the intermediate portion 6C of the linear member 6 comes to be in contact with the inner surface of the guiding tube 14. By configuring the return guide 9 in this manner, when the slider 4 is displaced in the axial direction x, the linear member 6 can be smoothly U-turned toward the distal side in the return guide 9.

The guiding tube 14 has flexibility and is preferably made of, for example, synthetic resin such as polyolefin resins (e.g., polyethylene or polypropylene), polyamide resins (e.g., nylon), polyester resins (e.g., PET), aromatic polyetherketone resins (e.g., PEEK), polyether polyamide resins, polyurethane resins, polyimide resins, and fluororesins (for example, PTFE, PFA, ETFE). Among these, the guiding tube 14 is preferably made of a highly slippery resin, and preferably made of fluororesin or polyolefin resin, more preferably made of fluororesin.

It is preferable that the guiding tube 14 has a first section 14A including one end, a second section 14B including the other end, and a third section 14C between the first section 14A and the second section 14B, at least a part of the third section 14C is held by the holding member 15, the first section 14A and the second section 14B are not held by the holding member 15, and the first section 14A and the second section 14B extend substantially parallel to the axial direction x distally from the holding member 15. By providing the guiding tube 14 in this manner, the linear member 6 can be smoothly introduced into or extended from the guiding tube 14 when the slider 4 is displaced in the axial direction x. That is, as the first section 14A and the second section 14B of the guiding tube 14 extend substantially parallel to the axial direction x, the linear member 6 tends to extend substantially parallel to the axial direction x from one end or the other end of the guide tube 14 toward the distal side. Furthermore, since the first section 14A and the second section 14B of the guiding tube 14 are not held by the holding member 15, even if the linear member 6 extends diagonally to the axial direction x, the first section 14A and the second section 14B can bend to follow it. Therefore, when the slider 4 is displaced in the axial direction x, the linear member 6 can be smoothly taken in and out of the guiding tube 14.

One end and the other end of the guiding tube 14 are determined based on the extending direction of the guiding tube 14, and the first section 14A and the second section 14B are located distal to the third section 14C in the state where the guiding tube 14 is held in a shape convex toward the proximal side. Therefore, the first section 14A and the second section 14B are defined as sections extending distally from the holding member 15 without being held by the holding member 15. The first section 14A and the second section 14B extending substantially parallel to the axial direction x distally from the holding member 15 means that the first section 14A and the second section 14B extend substantially parallel to the axial direction x in a plan view where the guiding tube 14 is seen in the shape convex toward the proximal side when no load is applied by the linear member 6.

As an embodiment in which the first section 14A and the second section 14B of the guiding tube 14 extend substantially parallel to the axial direction x, the first section 14A and the second section 14B of the guiding tube 14 preferably extend at an angle within ±10°, more preferably extend at an angle within ±5° to the axial direction x. The plus and minus of the angles represent clockwise and counterclockwise directions. The lengths of the first section 14A and the second section 14B of the guiding tube 14 are preferably 1 times or more, more preferably 2 times or more, and preferably 10 times or less, more preferably 7 times or less the outer diameter of the guiding tube 14.

The catheter handle of the present invention has been described above, but the catheter handle of the present invention is not limited to one which controls the bending of the distal end part of the tube, as long as it displaces the first and second portions of the linear member distally or proximally in the lumen of the tube. For example, the first portion and/or the second portion of the linear member may be moved in and out of the distal end of the tube by operating the catheter handle. Alternatively, a treatment tool such as a knife or a snare may be attached to the distal end of the first portion or the distal end of the second portion of the linear member and the treatment tool attached to the distal end of the first portion or the distal end of the second portion can be inserted or withdrawn from the distal end of the tube by operating the catheter handle.

This application claims priority to Japanese Patent Application No. 2021-201977 filed on Dec. 13, 2021, International Patent Application PCT/JP2022/034434 filed on Sep. 14, 2022, Japanese Patent Application No. 2023-047542 filed on Mar. 24, 2023, and Japanese Patent Application No. 2023-047543 filed on Mar. 24, 2023. All of the contents of the Japanese Patent Application No. 2021-201977 filed on Dec. 13, 2021, International Patent Application PCT/JP2022/034434 filed on Sep. 14, 2022, Japanese Patent Application No. 2023-047542 filed on Mar. 24, 2023, and Japanese Patent Application No. 2023-047543 filed on Mar. 24, 2023 are incorporated by reference herein.

REFERENCE SIGNS LIST

- 1: catheter handle
- 2: handle body
- 3: shaft
- 4: slider
- 5: rotary knob
- 6: linear member, 6A: first portion, 6B: second portion, 6C: intermediate portion
- 7: first connecting part
- 8: second connecting part
- 9: return guide
- 10: fixture (for linear member)
- 11: first annular part
- 12: second annular part
- 13: knot
- 14: guiding tube, 14A: first section, 14B: second section, 14C: third section
- 15: holding member
- 16: elongated hole (of holding member)
- 17: elongated hole (of handle body)
- 18: fixture (for return guide)
- 21: first engagement part
- 22: second engagement part
- 23: third engagement part
- 24: fourth engagement part
- 25: fifth engagement part
- 26: sixth engagement part
- 27: seventh engagement part
- 28: eighth engagement part
- 31: catheter
- 32: tube

The invention claimed is:

1. A catheter handle for operating a tube of a catheter, comprising:

a handle body having an inner cavity extending in an axial direction;

a shaft disposed in the inner cavity of the handle body, extending in the axial direction, and fixed to the handle body;

a slider disposed on an outside of the shaft, having a first engagement part extending spirally on an outer surface of the slider, and configured so as to be displaceable in the axial direction along the shaft;

a rotary knob provided so as to be rotatable around the axial direction relative to the handle body, and having a second engagement part on an inner surface of the rotary knob, which engages with the first engagement part of the slider;

a linear member having a first end and a second end, and having a first portion including the first end, a second portion including the second end, and an intermediate portion between the first portion and the second portion, the first portion and the second portion being disposed in a lumen of the tube, and the intermediate portion being disposed in the inner cavity of the handle body; and a return guide provided in the inner cavity of the handle body and being in contact at a contacting part of the linear member with at least a part of the intermediate portion of the linear member;

wherein the first portion and the second portion are composed of a metal wire, and the intermediate portion is composed of a fiber rope which is formed by twisting twisted yarns together to form strands and further twisting the strands together, and the linear member is fixed to the slider at a part of the linear member on the first end side from the contacting part of the linear member with the return guide.

2. The catheter handle according to claim 1, wherein the intermediate portion has lower bending rigidity than the first portion and the second portion.

3. The catheter handle according to claim 1, wherein one of the first engagement part and the second engagement part is a convex part and the other of the first engagement part and the second engagement part is a groove.

4. The catheter handle according to claim 1, wherein a proximal part of the first portion is connected to the intermediate portion at a first connecting part, a proximal part of the second portion is connected to the intermediate portion at a second connecting part, and the first connecting part and the second connecting part are located distal to a distal end of the slider in a state where the slider is displaced to a most distal side.

5. The catheter handle according to claim 4, wherein a proximal end of the first portion has a first annular part formed in an annular shape, and an end part of the intermediate portion on the first portion side is tied to the first annular part, thereby forming the first connecting part, and a proximal end of the second portion has a second annular part formed in an annular shape, and an end part of the intermediate portion on the second portion side is tied to the second annular part, thereby forming the second connecting part.

6. The catheter handle according to claim 5, wherein a knot formed by tying the end part of the intermediate portion on the first portion side to the first annular part and a knot formed by tying the end part of the intermediate portion on the second portion side to the second annular part are hardened with an adhesive or melt-solidified.

7. The catheter handle according to claim 4, wherein the intermediate portion is fixed to the slider at least at a distal one-third part of the slider.

8. The catheter handle according to claim 4, wherein the intermediate portion is fixed to the slider at least at a distal one-third part and a proximal one-third part of the slider.

9. The catheter handle according to claim 1, wherein the return guide is located proximal to the slider and configured to be fixable to the handle body at different positions in the axial direction.

10. The catheter handle according to claim 9, wherein an elongated hole extending in the axial direction is formed in the return guide, and a fixture for fixing the return guide is inserted through the elongated hole and is fitted or screwed into the handle body.

11. The catheter handle according to claim 9, wherein an elongated hole extending in the axial direction is formed in the handle body, and a fixture for fixing the return guide is inserted through the elongated hole and is fitted or screwed into the return guide.

12. The catheter handle according to claim 9, wherein the return guide comprises a guiding tube through which the intermediate portion of the linear member is inserted and which is arranged in a shape convex toward the proximal side, and a holding member which holds the guiding tube, and the holding member is configured to be fixable to the handle body at different positions in the axial direction.

13. The catheter handle according to claim 12, wherein the guiding tube has a first section including one end, a second section including the other end, and a third section between the first section and the second section, at least a part of the third section is held by the holding member, and the first section and the second section are not held by the holding member, and extend substantially parallel to the axial direction distally from the holding member in a plan view where the guiding tube is seen in the shape convex toward the proximal side.

14. The catheter handle according to claim 1, wherein the slider has a third engagement part on the outer surface of the slider, the handle body has a fourth engagement part on an inner surface of the handle body, which engages with the third engagement part, and at least one of the third engagement part and the fourth engagement part is provided so as to extend in the axial direction.

15. The catheter handle according to claim 1, wherein the slider has a fifth engagement part on an inner surface of the slider, the shaft has a sixth engagement part on an outer surface of the shaft, which engages with the fifth engagement part, and at least one of the fifth engagement part and the sixth engagement part is provided so as to extend in the axial direction.

16. A catheter comprising:

a catheter handle according to claim 1; and a tube provided on a distal side of the catheter handle.

* * * * *